(12) United States Patent
Coleman (10) Patent No.: US 10,758,474 B2
(45) Date of Patent: Sep. 1, 2020

(54) ORGANIC TOOTHPASTE

(71) Applicant: Radius Corporation, Kutztown, PA (US)

(72) Inventor: Saskia Coleman, Kutztown, PA (US)

(73) Assignee: Radius Corporation, Kutztown, PA (US)

( * ) Notice: Subject to any disclaimer, the term of this patent is extended or adjusted under 35 U.S.C. 154(b) by 0 days.

(21) Appl. No.: 16/345,242

(22) PCT Filed: Dec. 4, 2018

(86) PCT No.: PCT/US2018/063923
§ 371 (c)(1),
(2) Date: Apr. 25, 2019

(87) PCT Pub. No.: WO2019/231493
PCT Pub. Date: Dec. 5, 2019

(65) Prior Publication Data
US 2020/0121584 A1    Apr. 23, 2020

Related U.S. Application Data

(60) Provisional application No. 62/678,243, filed on May 30, 2018.

(51) Int. Cl.
| | | |
|---|---|---|
| A61K 8/97 | (2017.01) | |
| A61K 8/06 | (2006.01) | |
| A61K 8/34 | (2006.01) | |
| A61Q 11/00 | (2006.01) | |

(52) U.S. Cl.
CPC ............ *A61K 8/97* (2013.01); *A61K 8/062* (2013.01); *A61K 8/345* (2013.01); *A61Q 11/00* (2013.01); *A61K 2800/30* (2013.01); *A61K 2800/41* (2013.01); *A61K 2800/592* (2013.01)

(58) Field of Classification Search
CPC ............ A61K 8/97; A61K 8/55; A61Q 11/00
USPC ..................................................... 424/57
See application file for complete search history.

(56) References Cited

U.S. PATENT DOCUMENTS

| | | | |
|---|---|---|---|
| 4,071,614 A | 1/1978 | Grimm, III | |
| 5,294,434 A | 3/1994 | King et al. | |
| 5,723,107 A | 3/1998 | Blake-Haskins et al. | |
| 5,853,704 A | 12/1998 | Zhang et al. | |
| 6,126,923 A | 10/2000 | Burke et al. | |
| 6,485,711 B1 * | 11/2002 | Olmstead | A61K 8/922 424/49 |
| 6,998,112 B2 | 2/2006 | Zuckerman | |
| 8,715,625 B1 | 5/2014 | Rokitowski et al. | |
| 9,364,015 B2 | 6/2016 | Medoff | |
| 2004/0115138 A1 | 7/2004 | Healy et al. | |
| 2010/0303737 A1 | 12/2010 | Hurtig | |
| 2014/0017180 A1 * | 1/2014 | Isobe | A61K 8/55 424/57 |
| 2015/0209263 A1 | 7/2015 | Romanowski et al. | |

FOREIGN PATENT DOCUMENTS

| | | | | |
|---|---|---|---|---|
| CN | 103989596 | * | 8/2014 | ............ A61K 8/97 |
| CN | 103340778 B | | 11/2014 | |
| JP | 2007070256 A1 | | 3/2007 | |
| RU | 2431462 C1 | | 10/2011 | |
| WO | 18062605 A1 | | 4/2018 | |

OTHER PUBLICATIONS

Crunchy Urbanite, All-Natural Toothpaste, Apr. 16, 2014, https://thecrunchyurbanite.com/2014/04/16/all-natural-toothpaste/.
Mervat S. Hassanin, The effect of using Chamomile extract for the preservation of chicken breast meat on oxidative parameters and microbial profile of chicken meat, Oct. 24, 2015, African Journal of Agricultural Science and Technology (AJAST) vol. 3, Issue 10, pp. 419-424.ISSN 2311-5882.
Cristina Caleja, Development of a functional dairy food: exploring bioactive and preservation effects of chamomile, Jun. 16, 2015, Journal of Functional Foods.

* cited by examiner

*Primary Examiner* — Walter E Webb
(74) *Attorney, Agent, or Firm* — Invention To Patent Services; Alex Hobson (57) ABSTRACT

An organic toothpaste is a Pickering emulsion having a particle stabilizer bound in the interface between the continuous, phase and dispersed phase of the emulsion. The particle stabilizer prevents the dispersed phase from coalescing and phase separating. The emulsion may include glycerin and water to form the emulsion and particles, such as erythritol and/or rice powder as the stabilizer. An organic toothpaste may be certified USDA organic and contain no more than 5% by weight of components list of allowed substances, found in the Electronic Code of Federal Regulations, Subpart G published on May 24, 2018. An organic toothpaste may include a foaming component such as saponin, soapbark, decyl glucoside or *Quillaja saponaria*. In addition, an organic toothpaste may include a natural sweetener such as agave, xylitol or erythritol.

15 Claims, 3 Drawing Sheets

| Ingredient | Constituents | AS ADDED | Approximate Weight % | FUNCTION |
|---|---|---|---|---|
| Water | Water | 46.1290% | 46.1290% | hydrator |
| ORG Chamomile Concentrate | Water | | 6.6000% | botanical blend |
| | Chamomilla Recutita (Chamomile) Flower | 11.0000% | 4.4000% | |
| Organic Erythritol | Erythritol* | 12.0000% | 12.0000% | abrasive |
| ORG Rice Syrup Solids DE 2 | Oryza Sativa (Rice) | 0.1000% | 0.09500% | abrasive |
| | Water** | | 0.00500% | |
| Cocoganic | Coconut Water | 0.2000% | 0.1640% | conditioning agent |
| | Tapioca Maltodextrin* | | 0.0360% | |
| Organic Neem Extract | Glycerin* | | 0.00845% | conditioning agent |
| | Water | | 0.00075% | |
| | Melia Azadirachta | 0.0100% | 0.00075% | |
| CO Rose Extract | Glycerin* | | 0.00845% | conditioning agent |
| | Water | | 0.00075% | |
| | Rosa Centifolia (Rose) | 0.0100% | 0.00075% | |
| CO Hibiscus Extract | Glycerin* | | 0.00845% | conditioning agent |
| | Water | | 0.00075% | |
| | Hibiscus Sabdariffa | 0.0100% | 0.00075% | |
| CO Holy Basil Extract | Glycerin* | | 0.00845% | conditioning agent |
| | Water | | 0.00075% | |
| | Ocimum Sanctum (Holy | 0.0100% | 0.00075% | |
| Andean QDP Ultra | Quillaja Saponaria Wood | 0.2000% | 0.1920% | surfactant |
| | Citric Acid | | 0.0080% | |
| Aloe Vera 200x | Aloe Barbadensis (Aloe | 1.0200% | 1.0200% | conditioning |
| ORG Matcha | Camellia Sinensis (Green | 0.0100% | 0.0100% | conditioning |
| ORG Peppermint | Mentha Piperita | 0.5000% | 0.5000% | essential oil |
| Organic Rosemary Flavor | Ethyl Alcohol* | 0.1000% | 0.0980% | flavor |
| | Rosemary Oil* | | 0.0020% | |
| ORG Grapefruit Flavor | Ethyl Alcohol* | | 0.0610% | flavor |
| | Water | | 0.0350% | |
| | Pink Grapefruit Oil* | 0.1000% | 0.0040% | |
| ORG Green Tea Flavor | Ethyl Alcohol* | | 2.9120% | flavor |
| | Green Tea Essence* | | 0.1600% | |
| | Natural Ingredients | | 0.1280% | |
| | Lavender Extract* | 3.2000% | 0.0032% | |
| ORG Jasmine Flavor | Ethyl Alcohol* | | 0.9800% | flavor |
| | Natural Ingredients | | 0.0150% | |
| | Jasmine Extract* | 1.0000% | 0.0010% | |
| Nat ORG Toasted Almond Flavor | Ethyl Alcohol* | | 0.9600% | flavor |
| | Natural Ingredients | | 0.0400% | |
| | Coffee Espresso | 1.0000% | 0.0100% | |
| ORG Jasmine | Jasminum Grandiflorum | 0.0010% | 0.0010% | conditioning |
| ORG Guar Gum | Cyamopsis | 3.0000% | 3.0000% | thickener |
| Organic Glycerin | Glycerin* | 20.0000% | 20.0000% | humectant |
| Xanthan Gum | Xanthan Gum | 0.4000% | 0.4000% | thickener |

FIG. 3

ORGANIC TOOTHPASTE

CROSS REFERENCE TO RELATED APPLICATIONS

This application is a national stage entry of PCT/US2018/063923, filed on Dec. 4, 2018, and this application claims the benefit of U.S. provisional patent application No. 62/678,243, filed on May 30, 2018; the entirety of both applications are hereby incorporated by reference herein

BACKGROUND OF THE INVENTION

Field of the Invention

The invention relates to toothpaste and particularly to a United States Department of Agriculture (USDA) certified organic toothpaste comprising at least 95% by weight organic ingredients and no more than 5% of non-organic ingredients that are listed on the National Organic Program (NOP) list of allowed substances, found in the Electronic Code of Federal Regulations, Subpart G published on May 24, 2018.

Background

Many people are becoming more concerned about exposure to chemicals that may be detrimental to their health. Toothpaste comes in direct contact with the users mouth and to some degree is ingested, and or absorbed through the oral cavity. As a result, many people are turning to organic products including, food, soap, deodorant, shampoo and the like to reduce their exposure to harmful chemicals. For a product to be certified USDA organic it can contain no more than 5% by weight of non-organic materials and these materials have to be listed on the Code of Federal Regulations list of approved substances allowed as ingredients in or on products labeled as "organic" or "made with organic". The full list of these items is provided in Tables 3 to 5. The National List of Allowed and Prohibited Substances identifies the synthetic substances that may be used and the nonsynthetic (natural) substances that may not be used in organic crop and livestock production. It also identifies a limited number of non-organic substances that may be used in or on processed organic products as found on website: https://www.ams.usda.gov/rules-regulations/national-organic-program-national-list-allowed-and-prohibited-substances-crops https://www.ecfr.gov/cgi-bin/text-idx?c=ecfr&SID=9874504b6f1025eb0e6b67cadf9d3b40&rgn=div6&view=text&node=7:3.1.1.9.32.7&idno=7. For the purposes of this application the following versions of these list are to be used: § 205.605 Nonagricultural (nonorganic) substances allowed as ingredients in or on processed products labeled as "organic" or "made with organic (specified ingredients or food group(s)); and § 205.606 Nonorganically produced agricultural products allowed as ingredients in or on processed products labeled as "organic."

Toothpaste requires a very special set of characteristics that is very challenging to achieve and also meet the requirements of USDA organic. A toothpaste must have an effective consistency, have acceptable shelf life, have a pleasant taste and provide abrasive cleaning of the teeth and foam. This long list of attributes is very challenging to produce as a certified USDA organic product.

Toothpaste provides a wide variety of benefits including, but not limited to, cleaning debris and plaque from teeth and gums, whitening teeth, reducing bacteria, providing a pleasant taste and smell to the mouth and the like. Again, this long and diverse list of benefits in difficult to achieve with a single composition, especially one that is organic.

The National Organic Standards Board (NOSB) is designed by law to advise the National Organic Program (NOP) on which substances should be allowed or prohibited in products labeled USDA Certified Organic. The National Organic Program (NOP) is a regulatory program within the USDA Agricultural Marketing Service responsible for developing national standards for organically-produced agricultural products. Their standards are used to assure consumers that products with the USDA organic seal meet consistent, uniform standards.

SUMMARY OF THE INVENTION

The invention is directed to a USDA certified organic toothpaste comprising at least 95% by weight organic ingredients and no more than 5% of non-organic ingredients listed on the National List of Allowed and Prohibited Substances as detailed above. An exemplary USDA certified organic toothpaste, as used herein, has no more than 5% by weight of non-organic material and wherein these non-organic materials are selected from the list of substances allowed as ingredients in or on a product labeled as "Organic." A full list of the allowed non-organic substances is provided in Tables 5 to 8.

In an exemplary embodiment, the toothpaste comprises a Pickering emulsion, that has a continuous phase and a dispersed phase having an interface therebetween and particles bound within this interface that acts to stabilize the emulsion. One of the most difficult aspects of making a toothpaste out of organic ingredients is to form a suitable paste or gel having a viscosity that is high enough to allow the toothpaste to hold a shape when squeezed onto a toothbrush. In addition, the viscosity must not be too high as it may be difficult to dispense from the tube or other packaging. The viscosity of toothpaste at 20° C., may be from about 70 kcentipoise (cps) to about 500 kcps, or at least about 60 kcps, or at least about 70 kcps and no more than about 500 kcps, or no more than about 2500 kcps, and any range between and including, the values provided. In addition, the viscosity must be maintained over the shelf life of the product. Many emulsions phase separate over time which can dramatically drop the viscosity and make the product unsuitable for toothpaste. In a Pickering emulsion however, the particles within the interface prevent the dispersed phase from coalescing. The continuous phase in a Pickering emulsion may be water and the dispersed phase may be an oil, such as an organic fluid such as a glycerin, and/or the dispersed phase may be water, such as distilled water. The particles may comprise naturally derived organic particles such as erythritol, rice powder, coconut milk powder and/or coconut flour. The particles added in a Pickering emulsion may need to have a surface tension that is suitable to partially wet the continuous phase and dispersed phase. The particles may be of a size to enable effective stabilization of the Pickering emulsion. For example, the particles may be 20 mesh or no more than about 850 microns in size, about 30 mesh or no more than about 600 microns in size, about 40 mesh or no more than about 400 microns in size, 50 mesh or no more than about 300 microns is size, or any range between and including the particle sizes provided. Rice powder for example may be 50 mesh. In addition, the fatty acids derived from other ingredients may act to stabilize the Pickering emulsion.

An exemplary USDA certified organic toothpaste comprises a hydrator or water component, oil to produce an emulsion with the water component, humectant to reduce moisture loss, abrasive for effective cleaning, particles to stabilize the Pickering emulsion, preservative, flavoring and a conditioning agent. Obtaining all of these ingredients in the correct concentrations to achieve all of the required properties and be USDA certified organic is very challenging. An exemplary USDA certified organic toothpaste may not utilize an oil and the consistency may be achieved through the mixture of the other components as described or with a substitute to oil to produce the emulsion.

Table 1 provides an exemplary toothpaste formulation that qualifies as USDA Certified Organic and has all of the properties required for a toothpaste including shelf life. Water and glycerin are mixed with particles including erythritol and rice powder to form a Pickering emulsion. Glycerin may also act as a humectant to prevent water loss and any number of flavors can be added from natural sources such as jasmine extract, grapefruit oil and the like. Glycerin may form the dispersed, or discontinuous phase in the Pickering emulsion. Chamomile may be added and act as a natural preservative and an exemplary Chamomile extract is available from Naturally Sourced Solutions, Naples, Fla. The abrasive may be particles of erythritol and rice powder.

The continuous phase of the Pickering emulsion may be formed by water. Water may be added in a relatively high concentration by weight of the toothpaste formulation, such as about 30% or more, about 40% of more, about 50% or more about 60% or more, about 70% or less and any of the concentrations provided herein. It is surprising that a formulation with such high concentrations of water can maintain viscosity overtime and not phase separate.

The particles of the Pickering emulsion may be erythritol, rice powder, or coconut flour, or powder. The particles may be added in a concentration by weight of the toothpaste formulation, such as about 5% or more, about 8% of more, about 10% or more about 15% or more, about 20% or less and any of the concentrations provided herein. The particles may also act as an abrasive for effective cleaning of teeth. Erythritol also is sugar alcohol and a sweetener for the toothpaste. Erythritol is 60-70% as sweet as sucrose but has very low calories and does not affect blood sugar or cause tooth decay. Furthermore, erythritol has low solubility, as it has no reducing end groups. There are studies that show that Erythritol fights bacteria and can help to prevent cavities. Erythritol is not hygroscopic and has a lower water solubility than sucrose and a higher tendency to crystallize. An exemplary Erythritol is Organic Erythritol, 20-30 mesh size, available from Pyure, Naples, Fla.

TABLE 1

| Ingredient | Constituents | AS ADDED | Approximate Weight % | FUNCTION |
|---|---|---|---|---|
| Water | Water | 46.1290% | 46.1290% | hydrator |
| ORG Chamomile Concentrate | Water | 11.0000% | 6.6000% | botanical blend |
|  | *Chamomilla Recutita* (Chamomile) Flower |  | 4.4000% |  |
| Organic Erythritol | Erythritol* | 12.0000% | 12.0000% | abrasive |
| ORG Rice Syrup Solids DE 2 | *Oryza Sativa* (Rice) | 0.1000% | 0.09500% | abrasive |
|  | Water** |  | 0.00500% |  |
| Cocoganic | Coconut Water | 0.2000% | 0.1640% | conditioning agent |
|  | Tapioca Maltodextrin* |  | 0.0360% |  |
| Organic Neem Extract | Glycerin * | 0.0100% | 0.00845% | conditioning agent |
|  | Water |  | 0.00075% |  |
|  | *Melia Azadirachta* |  | 0.00075% |  |
| CO Rose Extract | Glycerin * | 0.0100% | 0.00845% | conditioning agent |
|  | Water |  | 0.00075% |  |
|  | *Rosa Centifolia* (Rose) |  | 0.00075% |  |
| CO Hibiscus Extract | Glycerin* | 0.0100% | 0.00845% | conditioning agent |
|  | Water |  | 0.00075% |  |
|  | *Hibiscus Sabdariffa* |  | 0.00075% |  |
| CO Holy Basil Extract | Glycerin * | 0.0100% | 0.00845% | conditioning agent |
|  | Water |  | 0.00075% |  |
|  | *Ocimum Sanctum* (Holy |  | 0.00075% |  |
| Andean QDP Ultra | *Quillaja Saponaria* Wood | 0.2000% | 0.1920% | surfactant |
|  | Citric Acid |  | 0.0080% |  |
| Aloe Vera 200x | *Aloe Barbadensis* (Aloe | 1.0200% | 1.0200% | conditioning |
| ORG Matcha | *Camellia Sinensis* (Green | 0.0100% | 0.0100% | conditioning |
| ORG Peppermint | *Mentha Piperita* | 0.5000% | 0.5000% | essential oil |
| Organic Rosemary Flavor | Ethyl Alcohol* | 0.1000% | 0.0980% | flavor |
|  | Rose mary Oil* |  | 0.0020% |  |
| ORG Grapefruit Flavor | Ethyl Alcohol * | 0.1000% | 0.0610% | flavor |
|  | Water |  | 0.0350% |  |
|  | Pink Grapefruit Oil* |  | 0.0040% |  |
| ORG Green Tea Flavor | Ethyl Alcohol* | 3.2000% | 2.9120% | flavor |
|  | Green Tea Essence* |  | 0.1600% |  |
|  | Natural ingredients |  | 0.1280% |  |
|  | Lavender Extract* |  | 0.0032% |  |
| ORG Jasmine Flavor | Ethyl Alcohol* | 1.0000% | 0.9800% | flavor |
|  | Natural Ingredients |  | 0.0150% |  |
|  | Jasmine Extract* |  | 0.0010% |  |
| Nat ORG Toasted Almond Flavor | Ethyl Alcohol* | 1.0000% | 0.9600% | flavor |
|  | Natural ingredients |  | 0.0400% |  |
|  | Coffee Espresso |  | 0.0100% |  |
| ORG Jasmine | *Jasminum Grandiflorum* | 0.0010% | 0.0010% | conditioning |
| ORG GuarGum | *Cyamopsis* | 3.0000% | 3.0000% | thickener |
| Organic Glycerin | Glycerin* | 20.0000% | 20.0000% | humectant |
| Xanthan Gum | Xanthan Gum | 0.4000% | 0.4000% | thickener |

Other natural oils may be added to the toothpaste formulation as flavoring or to contribute to the dispersed phase of the Pickering emulsion. Some natural oils are provided in Table 2. Aloe may be added to the toothpaste formulation as a concentrate to avoid separation. A concentrated powder of aloe may be reconstituted with water before adding to the toothpaste formulation. An exemplary Aloe Vera concentrate is available from Terry Laboratories, Melbourne, Fla. and is a 200× concentrate. Aloe is very good for gum health.

An exemplary organic toothpaste may include a surfactant or foaming component that is naturally derived and/or organic, such as saponin, which is found in agave and the yucca plant. Other natural surfactants or foaming components include, but are not limited to, Soapbark (*Quillaja saponaria*) and decyl glucoside (Plantaren). Plantaren, is an alkyl polyglucoside, a non-ionic surfactant obtained from renewable, plant-derived raw materials. *Quillaja saponaria* may be preferred foaming agent.

An exemplary organic toothpaste may comprise natural or naturally derived sweeteners including, but not limited to, agave, yawn syrup, derived from the yucca plant, erythritol, xylitol, natural sugars, and the like. Xylitol is categorized as a polyalcohol or sugar alcohol (alditol). Xylitol is naturally found in low concentrations in a variety of natural sources including fruits and vegetables, berries, oats, as well as fibrous material such as corn husks and sugar cane bagasse. Xylitol may be preferred as it is actively beneficial for dental health as it is a nonfermentable sugar alcohol. Xylitol contains a tridentate ligand, $(H\!-\!C\!-\!OH)_3$ that rearranges with polyvalent cations like $Ca^{2+}$, transported through the through saliva, to allow enamel to remineralize before dental cavities form. Erythritol is a sugar alcohol or polyol, and does not provide as many calories as sugar, is 60-70% as sweet as sucrose, yet has very few calories and does not affect blood sugar. Erythritol is found in some fruits and fermented foods and is produced from glucose by fermentation with a yeast. Erythritol also does not cause tooth decay. Sweetener may be added in a concentration of about 5% to 20% by weight. The agave and yacon syrup contain saponin which is a natural surfactant, soaping or foam forming agent and therefore may be added in higher concentrations as they are dual purpose. In one embodiment, the sweetener is xylitol or erythritol and the soaping agent is an alkyl polyglucoside, such as decyl glucoside (Plantaren). A sweetener may be added in relatively high concentrations such as about 5% or more by weight, about 8% or more by weight, about 10% or more by weight, about 12% or more by weight, about 20% or less by weight and any range between and including the weight percentages provided. A preferred sweetener is Erythritol for the reasons provided herein and Erythritol may also acts as particles for an abrasive and to stabilize the Pickering Emulsion. Erythritol may also be an exfoliant.

An exemplary organic toothpaste may comprise one or more natural or naturally derived flavoring components including, but not limited to, ginger powder, eucalyptus oil, fruit or berry oils or extracts including, but not limited to, orange oil, raspberry, banana, lemon, coconut, apple or apple extract, grapefruit, neem oil, and herbal components including, but not limited to, hibiscus, rosemary, tea tree, horse tail, peppermint oil, mint leaves or mint extract, holy basil, neem and/or rose hips. An exemplary neem component is an organic neem extract in organic glycerin and water. An exemplary neem is available from Carrubba, Inc., Milford, Conn.

An exemplary organic toothpaste may also comprise a thickening agent such as guar gum, xanthan gum and the like. Thickening agents may be added in a concentration of about 3% or more by weight, about 4% or more by weight, about 5% or more by weight and any range between and including the weight percentages provided. or humectants including, but not limited to, glycerin, aloe vera, yacon syrup and agave syrup. A humectant may be a key ingredient to enable a toothpaste to achieve a required shelf-life. Glycerin or another humectant may be added in relatively high concentrations for this purpose, as described herein.

For a product to be certified USDA organic, the product may contain no more than 5% of material by weight that is non-organic, and these materials must be on the allowed substances list, provided herein. As required by the USDA, any water and salt included in the product must be removed from the equation for determination of the weight percent of non-organic materials. In an exemplary embodiment, the toothpaste is certified USDA organic and contains no more than 5% by weight non-organic materials, and preferably contains no more than 4% by weight non-organic material, and more preferably contains only certified organic materials, as defined by the USDA.

In an exemplary embodiment, the organic toothpaste contains no more than 5% by weight of any of the materials or combination of materials listed in Tables 3 to 5, or on any future list of allowed substances for inclusion in a certified organic product by the USDA.

In an exemplary embodiment, an organic toothpaste, or the Pickering emulsion, contains glycerin in a concentration of at least about 10%, at least about 15%, at least about 20%, at least about 25%, at least about 30% by weight, at least about 35% by weight of the organic toothpaste or any concentration between and including the percent concentrations provided. The organic toothpaste or the Pickering emulsion contains water, such as distilled water, in a concentration of at least about 30%, at least about 35%, at least about 40%, at, least about 50% by weight, at least about 55%, at least about 60% by weight of the organic toothpaste or any concentration between and including the percent concentrations provided. The ratio of the water to glycerin may be important in the formation of the emulsion and therefore the ratio may be about 1.5:1 or more, about 2:1 or more, about 2.5:1 or more, about 3:1 or more and any range between and including the ratios provided. The concentration of water may be relatively high in the toothpaste formulation, which is surprising given all the other properties the formulation must have. Xatham gum is a very strong thickening agent and guar gum may be added to further stabilize and thicken the composition.

An exemplary organic toothpaste may comprise a particle stabilizer that attaches to the interface of the continuous and dispersed phase, or discontinuous phase of the emulsion to prevent phase separation and includes, but is not limited to, Erythritol, rice powder, coconut milk powder, coconut flour, calcium carbonate, sodium bicarbonate and the like. Erythritol may be a preferred stabilizer as it has relatively low solubility in water and therefore may be provided in a relatively high concentration, such as about 10% by weight or more, about 12% by weight or more, about 15% by weight or more, about 18% by weight or more, about 20% by weight or more about 25% by weight or more and any range between and including the percentages provided. Erythritol and/or rice powder may be included in the Pickering emulsion in a concentration sufficient to provide adequate stabilization of the emulsion, as described herein.

TABLE 3

Nonagricultural Substances Allowed (a) Nonsynthetics allowed:
Acids (Alginic; Citric - produced by microbial fermentation of carbohydrate substances; and Lactic).
Agar-agar.
Animal enzymes - (Rennet - animals derive; Catalase - bovine liver; Animal lipase;
Attapulgite - as a processing aid in the handling of plant and animal oils.
Bentonite.
Calcium carbonate.
Calcium chloride.
Calcium sulfate - mined.
Carrageenan.
Dairy cultures.
Diatomaceous earth - food filtering aid only.
Enzymes - must be derived from edible, nontoxic plants, nonpathogenic fungi; or
Flavors, nonsynthetic sources only and must not be produced using synthetic solvents and
Gellan gum (CAS # 71010-52-1) - high-acyl form only.
Glucono delta-lactone - production by the oxidation of D-glucose with bromine water is
Kaolin.
L-Malic acid (CAS # 97-67-6).
Magnesium sulfate, nonsynthetic sources only.
Microorganisms - any food grade bacteria, fungi, and other microorganism.
Nitrogen - oil-free grades.
Oxygen - oil-free grades.
Perlite - for use only as a filter aid in food processing.
Potassium chloride.
Potassium iodide.
Sodium bicarbonate.
Sodium carbonate.
Tartaric acid - made from grape wine.
Waxes - nonsynthetic (Carnauba wax; and Wood resin).
Yeast - When used as food or a fermentation agent in products labeled as "organic," yeast must be organic if its end use is for human consumption; nonorganic yeast may be used when organic yeast is not commercially available. Growth on petrochemical substrate and sulfite waste liquor is prohibited. For smoked yeast, nonsynthetic smoke flavoring process must be documented.

TABLE 4

Synthetics Allowed (b) Synthetics allowed:
Acidified sodium chlorite - Secondary-direct antimicrobial food treatment and indirect food contact surface sanitizing.
Acidified with citric acid only.
Activated charcoal (CAS #s 7440-44-0; 64365-11-3) - only from vegetative sources: for use only as a filtering aid.
Alginates.

TABLE 4-continued

Synthetics Allowed

Ammonium bicarbonate - for use only as a leavening agent.
Ammonium carbonate - for use only as a leavening agent.
Ascorbic acid.
Calcium citrate.
Calcium hydroxide.
Calcium phosphates (monobasic, dibasic, and tribasic).
Carbon dioxide.
Cellulose - for use in regenerative casings, as an anti-caking agent (non-chlorine bleached) and filtering aid.
Chlorine materials - disinfecting and sanitizing food contact surfaces, Except, That, residual chlorine levels in the water shall not exceed the maximum residual disinfectant limit under the Safe Drinking Water Act (Calcium hypochlorite;
Chlorine dioxide; and Sodium hypochlorite).
Ethylene - allowed for postharvest ripening of tropical fruit and degreening of citrus.
Ferrous sulfate - for iron enrichment or fortification of foods when required by regulation or recommended (independent organization).
Glycerides (mono and di) - for use only in drum drying food.
Glycerin - produced by hydrolysis of fats and oils.
Hydrogen peroxide.
Magnesium chloride - derived from sea water.
Magnesium stearate - for use only in agricultural products labeled "made with organic (specified ingredients or food group(s))," prohibited in agricultural products labeled "organic".
Nutrient vitamins and minerals, in accordance with 21 CFR 104.20, Nutritional Quality Guidelines For Foods.
Ozone.
Peracetic acid/Peroxyacetic acid (CAS # 79-21-0) - for use in wash and/or rinse water according to FDA limitations.
For use as a sanitizer on food contact surfaces.
Phosphoric acid - cleaning or food-contact surfaces and equipment only.
Potassium acid tartrate.
Potassium carbonate.
Potassium citrate.
Potassium hydroxide - prohibited for use in lye peeling of fruits and vegetables except when used for peeling peaches.
Potassium phosphate - for use only in agricultural products labeled "made with organic (specific ingredients or food group(s))," prohibited in agricultural products labeled "organic".
Silicon dioxide - Permitted as a defoamer. Allowed for othe uses when organic rice hulls are not commercially available.
Sodium acid pyrophosphate (CAS # 7758-16-9) - for use only as a leavening agent.
Sodium citrate.
Sodium hydroxide - prohibited for use in lye peeling of fruits and vegetables.
Sodium phosphates - for use only in dairy foods.
Sulfur dioxide - for use only in wine labeled "made with organic grapes," Provided, That, total sulfite concentration does not exceed 100 ppm.
Tocopherols - derived from vegetable oil when rosemary extracts are not a suitable alternative.
Xanthan gum.

TABLE 5

Non-organically produced agricultural products allowed (a) Casings, from processed intestines.
(b) Celery powder.
(c) Colors derived from agricultural products - Must not be produced using synthetic solvents and carrier systems or any artificial preservative.
(1) Beet juice extract color (pigment CAS #7659-95-2).
(2) Beta-carotene extract color - derived from carrots or algae (pigment CAS# 7235-40-7).
(3) Black currant juice color (pigment CAS #'s; 528-58-5, 528-53-0, 643-84-5, 134-01-0, 1429-30-7, and 134-04-3).
(4) Black/Purple carrot juice color (pigment CAS #'s: 528-58-5, 528-53-0, 643-84-5, 134-01-0, 1429-30-7, and 134-04-3).
(5) Blueberry juice color (pigment CAS #'s: 528-58-5, 528-53-0, 643-84-5, 134-01-0, 1429-30-7, and 134-04-3).
(6) Carrot juice color (pigment CAS #1393-63-1).
(7) Cherry juice color (pigment CAS #'s: 528-58-5, 528-53-0, 643-84-5, 134-01-0, 1429-30-7, and 134-04-3).

TABLE 5-continued

Non-organically produced agricultural products allowed (8) Chokeberry - Aronia juice color (pigment CAS #'s: 528-58-5, 528-53-0, 643-84-5, 134-01-0, 1429-30-7, and 134-04-3).
(9) Elderberry juice color (pigment CAS #'s: 528-58-5, 528-53-0, 643-84-5, 134-01-0, 1429-30-7, and 134-04-3).
(10) Grape juice color (pigment CAS #'s: 528-58-5, 528-53-0, 645-84-5, 134-01-0, 1429-30-7, and 134-04-3).
(11) Grape skin extract color (pigment CAS #'s: 528-58-5, 528-53-0, 643-84-5, 134-01-0, 1429-30-7, and 134-04-3).
(12) Paprika color (CAS #68917-78-2) - dried, and oil extracted.
(13) Pumpkin juice color (pigment CAS #127-40-2).
(14) Purple potato juice (pigment CAS #'s: 528-58-5, 528-53-0, 643-84-5, 134-01-0, 1429-30-7, and 134-04-3).
(15) Red cabbage extract color (pigment CAS #'s: 528-58-5, 528-53-0, 643-84-5, 134-01-0, 1429-30-7, and 134-04-3).
(16) Red radish extract color (pigment CAS #'s: 528-58-5, 528-53-0, 643-84-5, 134-01-0, 1429-30-7, and 134-04-3).
(17) Saffron extract color (pigment CAS #1393-63-1).
(18) Turmeric extract color (CAS #458-37-7).
(d) Fish oil (Fatty acid CAS #'s: 10417-94-4, and 25167-62-8) - stabilized with organic ingredients or only with ingredients on the National List, ♦♦205.605 and 205.606.
(e) Fructooligosaccharides (CAS # 308066-66-2).
(f) Gelatin (CAS # 9000-70-8).
(g) Gums - water extracted only (Arabic; Guar; Locust bean; and Carob bean).
(h) Inulin - oligofructose enriched (CAS # 9005-80-5).
(i) Kelp - for use only as a thickener and dietary supplement.
(j) Konjac flour (CAS # 37220-17-0).
(k) Lecithin - de-oiled.
(l) Orange pulp, dried.
(m) Orange shellac-unbleached (CAS # 9000-59-3).
(n) Pectin (non-amidated forms only).
(o) Seaweed, Pacific kombu.
(p) Starches.
(1) Cornstarch (native).
(2) Sweet potato starch - for bean thread production only.
(q) Tragacanth gum (CAS #-9000-65-1).
(f) Turkish bay leaves.
(s) Wakame seaweed (Undaria pinnatifida).
(t) Whey protein concentrate.

An exemplary organic toothpaste of the present invention has a suitable viscosity at 20° C., such as about 100,000 centipoise to about 1,000,000 centipoise and more preferably between about 100,000 to 500,000 centipoise, and is stable over the required shelf life of two years. An exemplary organic toothpaste of the present invention has a pleasant taste and has particles to provide effective cleaning and whitening of teeth. An exemplary organic toothpaste of the present invention produces soap and foams. An exemplary organic toothpaste of the present invention has a pleasant smell and leaves a person's mouth feeling clean and fresh after use.

An exemplary toothpaste may be formed by first mixing the abrasives or particle components with water and then adding a surfactant or foaming agent and subsequently adding flavoring. The flavorings may be premixed before adding to the composition. The composition may be heated during the process to enhance mixing and dispersion of ingredients. Thickeners and the oil component may be added to the composition and mixed at a high rate to form the Pickering Emulsion. The oil or discontinuous component may be glycerin and this may be premixed with the thickener, such as xanthan gum and/or guar gum prior to mixing with the composition.

The summary of the invention is provided as a general introduction to some of the embodiments of the invention and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 3 shows an exemplary toothpaste formulation.

DETAILED DESCRIPTION OF THE ILLUSTRATED EMBODIMENTS

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

Figure 1:
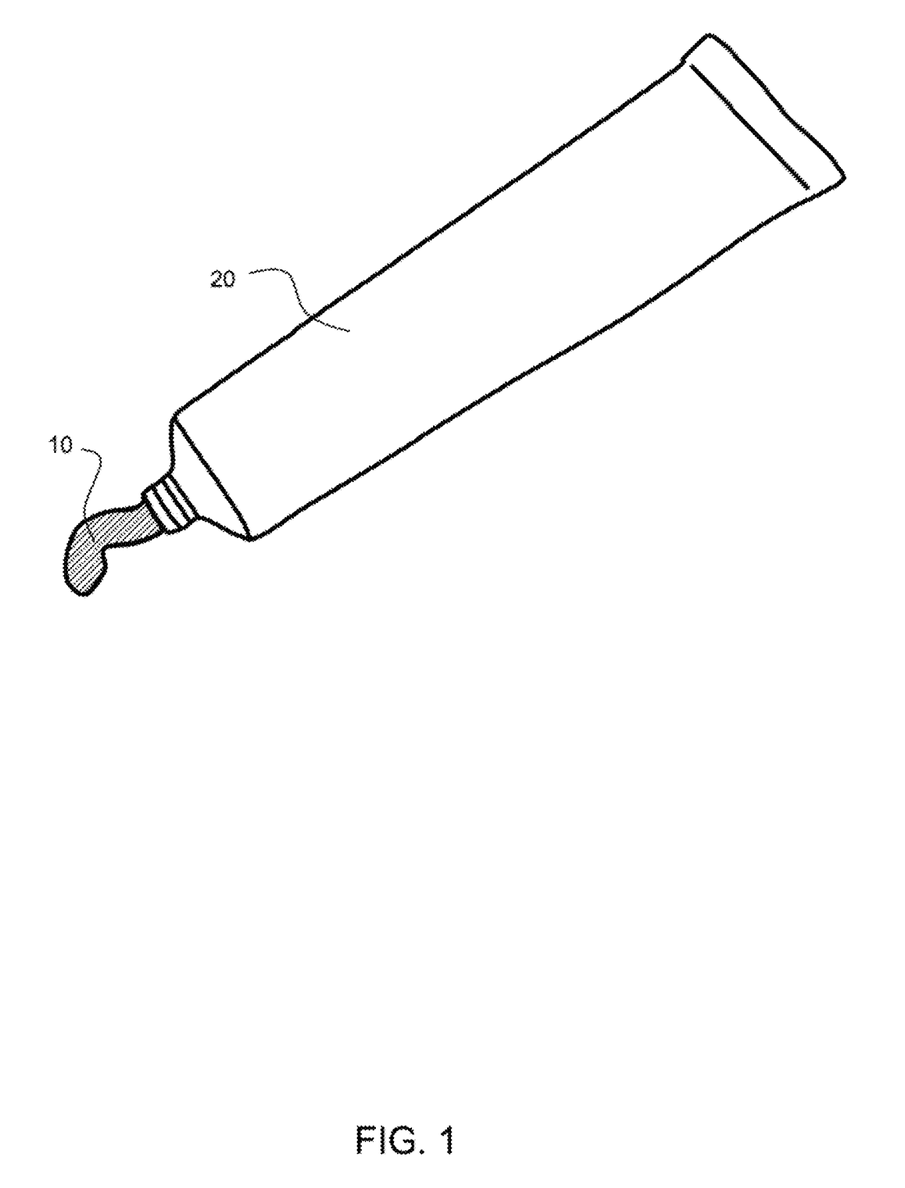
FIG. 1 shows a toothpaste tube and toothpaste being dispensed from said tube.

As shown in FIG. 1, a certified USDA organic toothpaste 10 is being dispensed from a toothpaste tube 20.

Figure 2:
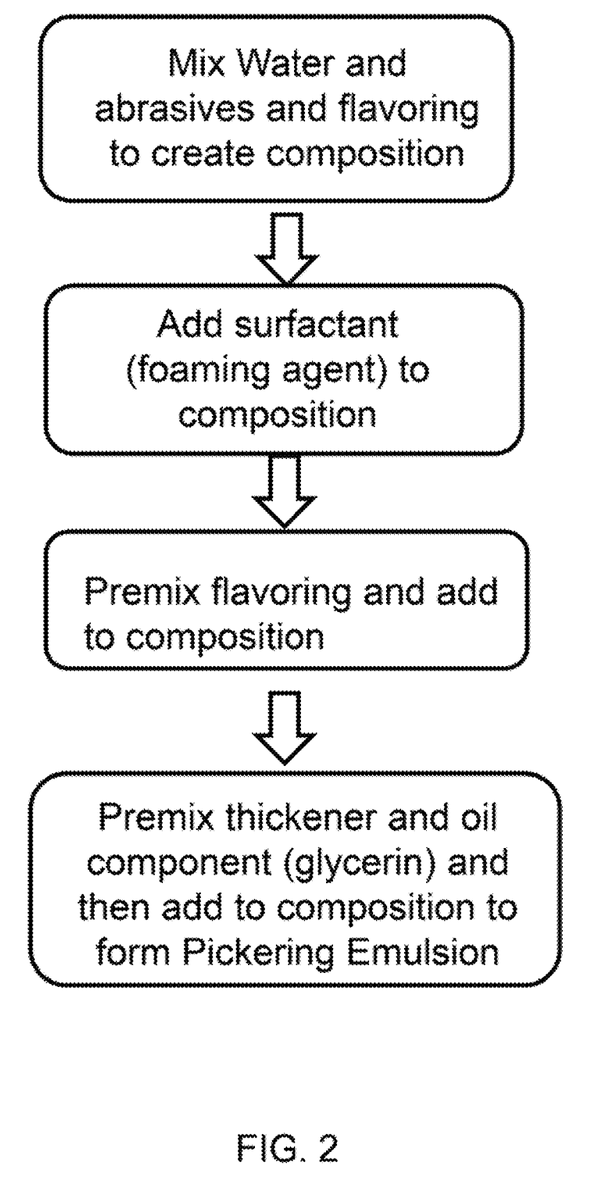
FIG. 2 shows a flow diagram of a process method to make an organic toothpaste that comprises a Pickering emulsion.

As shown in FIG. 2, the Pickering emulsion is formed by first mixing the components the continuous phase with the particles. In this exemplary embodiment, water is mixed with the particles, erythritol and rice powder. Other extracts may also be combined with this initial composition and mixed. Flavoring may be, premixed and then added to the continuous phase composition. Thickening components as well as the discontinuous phase components may be premixed and then added to the continuous phase composition and mixed vigorously to form an emulsion, a Pickering emulsion wherein particles, erythritol are within the interface between the continuous and discontinuous or dispersed phase. In an exemplary embodiment, the discontinuous phase consists essentially of glycerin, wherein the discontinuous phase is at least 75% glycerin and preferably is at least 85% glycerin.

As shown in FIG. 3, a USDA certified organic toothpaste formulation contains no more than 5% of non-organic ingredients provided on the list of allowed substances, found in the Electronic Code of Federal Regulations, Subpart G published on May 24, 2018. This exemplary formulation, when mixed and combined in an effective way, achieves all of the required properties of toothpaste including, viscosity, foaming, abrasive, flavor and shelf-life.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

The following references are incorporated herein by reference in their entirety:

Reference 1: Nattapol Tangsuphoom, August (2008). Properties and Structures Of Coconut Milk Emulsions, A Dissertation in Food Science. The Pennsylvania State University, The Graduate School, College of Agricultural Sciences, ProQuest LLC;

Reference 2: Nazima Siddiqui, Adeel Ahmad, (2013). A STUDY ON VISCOSITY, SURFACE TENSION AND VOLUME FLOW RATE OF SOME EDIBLE AND MEDICINAL OILS, Biophysics Research Laboratory, Department of Physics, Nizam College, Osmania University, Hyderabad-500 001, India, International Journal of Science, Environment and Technology, Vol. 2 No 6, 1318-1326, ISSN 2278-3687 (O).

Reference 3: J. González1, C. Albano2, M. Hernández1, M. N. Ichazo1, S. Alvarado2, D. M. Ziegler, (2001), MECHANICAL PROPERTIES AND MORPHOLOGY OF POLYOLEFIN COMPOSITES WITH COCONUT FLOUR, 1Universidad Simón Bolivar. Departamento de Mecánica, Caracas-Venezuela and 2Universidad Central de Venezuela, Escuela de Ing. Quimica, Caracas-Venezuela

What is claimed is:

1. An organic toothpaste, wherein the toothpaste is organic as defined by comprising at least 95% by weight of organic ingredients derived from living organisms and no more than 5% by weight of ingredients on the list of allowed substances, found in the Electronic Code of Federal Regulations, Subpart G published on May 24, 2018; wherein the organic toothpaste comprises:
    a) at least 40% by weight water;
    b) at least 8% by weight chamomile flower extract to preserve the USDA certified organic toothpaste; and
    c) an abrasive comprising Erythritol;
    d) a natural foaming ingredient;
    wherein the toothpaste is a Pickering emulsion comprising:
        i. a continuous phase of said emulsion comprising water;
        ii. a dispersed phase of the emulsion comprising glycerin in a concentration of at least 15% by weight of the organic toothpaste;
        iii. an interface between said continuous and dispersed phase of the emulsion;
        iv. a particle stabilizer located in said interface to stabilize the emulsion, wherein the particle stabilizer has a particle size of no more than 850 microns; and
    the organic toothpaste has a viscosity at 20° C. between 60 kcps and 500 kcps (could use 2500 kcps as upper limit); and
    wherein the organic toothpaste has a shelf life of at least 12 months wherein the viscosity is maintained between 60 kcps and 500 kcps.

2. The organic toothpaste of claim 1, wherein the USDA certified organic toothpaste contains only no non-organic preservatives.

3. The organic toothpaste of claim 1, wherein the Erythritol is included in a concentration by weight of at least 8%.

4. The organic toothpaste of claim 1, wherein the natural foaming ingredient is *Quillaja Saponaria*.

5. The organic toothpaste of claim 1, wherein the continuous phase comprises water.

6. The organic toothpaste of claim 5, wherein the water is included in a concentration of at least 50% by weight of the organic toothpaste.

7. The organic toothpaste of claim 1, wherein the dispersed phase consists essentially of glycerin.

8. The organic toothpaste of claim 7, wherein the glycerin is included in a concentration of at least 15% by weight of the organic toothpaste.

9. The organic toothpaste of claim 8, wherein the water and glycerin are present in the Pickering emulsion in a concentration ratio of water to glycerin of at least 2 to 1.

10. The organic toothpaste of claim 8, wherein the water and glycerin are present in the Pickering emulsion in a concentration ratio of water to glycerin of at least 1.5 to 1.

11. The organic toothpaste of claim 1, wherein the stabilizer comprises erythritol.

12. The organic toothpaste of claim 11, wherein erythritol has a particle size of no more than 850 microns.

13. The organic toothpaste of claim 1, wherein the stabilizer consists essentially of erythritol, wherein at least 75% of the particles in the organic toothpaste are erythritol.

14. The organic toothpaste of claim 1, further comprising a sweetener and wherein the sweetener comprises erythritol.

15. The organic toothpaste of claim 14, wherein the sweetener consists essentially of erythritol wherein at least 85% of the sweetener is erythritol.

* * * * *